US012731478B1

(12) United States Patent
Tammana

(10) Patent No.: US 12,731,478 B1
(45) Date of Patent: Sep. 8, 2026

(54) COMPUTER-IMPLEMENTED SYSTEM AND METHOD FOR GENERATING REMINDERS FOR USERS USING A SCREENLESS WEARABLE DEVICE

(71) Applicant: Sri Nihal Tammana, Monroe Township, NJ (US)

(72) Inventor: Sri Nihal Tammana, Monroe Township, NJ (US)

(73) Assignee: Sri Nihal Tammana

( * ) Notice: Subject to any disclaimer, the term of this patent is extended or adjusted under 35 U.S.C. 154(b) by 0 days.

(21) Appl. No.: 19/649,494

(22) Filed: Apr. 16, 2026

(51) Int. Cl.
*G08B 21/24* (2006.01)
*A61B 5/00* (2006.01)
(Continued)

(52) U.S. Cl.
CPC .......... *G08B 21/24* (2013.01); *A61B 5/02438* (2013.01); *A61B 5/681* (2013.01);
(Continued)

(58) Field of Classification Search
CPC ............... G06F 11/263; G06F 11/3684; G06F 16/9538; G06F 16/9577;
(Continued)

(56) References Cited

U.S. PATENT DOCUMENTS

2005/0200883 A1* 9/2005 Mannion ............... G06F 3/1231 358/1.15
2006/0074658 A1* 4/2006 Chadha ................... G10L 17/00 704/E15.045

(Continued)

FOREIGN PATENT DOCUMENTS

CN 205232214 U 5/2016
IN 201941054851 A 1/2020

OTHER PUBLICATIONS https://in.amazfit.com/products/helio-strap?srsltid=AfmBOoqJy2P-kmWfGdGH6nxbFJzUR9-3_EEUXhdHCRclimh65jhlX5F; Title: Helio strap.

(Continued)

*Primary Examiner* — Daniel Previl
(74) *Attorney, Agent, or Firm* — Jason C. Cameron

(57) ABSTRACT

A computer-implemented method and system for generating reminder using a screenless wearable device, is disclosed. The screenless wearable device is configured to activate, by a microcontroller unit (MCU), a microphone to execute press-to-listen interaction in response to users providing the inputs through input button. The screenless wearable device is further configured to capture, by the microphone, natural speech of the users during a pre-defined time duration. The screenless wearable device is further configured to analyze, by the MCU, pre-defined code words and phrases from captured natural speech. The screenless wearable device is further configured to transmit, by the transceiver, an audio associated with natural speech to communication devices through communication technologies. The communication devices are configured to generate reminders based on the audio associated with natural speech, using an AI model. The screenless wearable device is further configured to deliver generated reminders to the users through haptic vibrations.

20 Claims, 4 Drawing Sheets

(51) Int. Cl.

| | |
|---|---|
| ***A61B 5/024*** | (2006.01) |
| ***G06F 40/295*** | (2020.01) |
| ***G06F 40/30*** | (2020.01) |
| ***G08B 7/06*** | (2006.01) |
| ***G10L 15/18*** | (2013.01) |
| ***G10L 15/22*** | (2006.01) |
| ***G10L 15/30*** | (2013.01) |
| ***G10L 25/60*** | (2013.01) |
| *G10L 15/08* | (2006.01) |

(52) U.S. Cl.
CPC .......... *A61B 5/7405* (2013.01); *A61B 5/7455* (2013.01); *G06F 40/295* (2020.01); *G06F 40/30* (2020.01); *G08B 7/06* (2013.01); *G10L 15/1815* (2013.01); *G10L 15/22* (2013.01); *G10L 15/30* (2013.01); *G10L 25/60* (2013.01); *G10L 2015/088* (2013.01)

(58) Field of Classification Search
CPC ......... G06F 2203/04808; G06F 3/0482; G06F 3/0485; G06F 3/0488; G06F 3/04883; G06F 3/1203; G06F 3/1204; G06F 3/1231; G06F 3/1286; G06F 3/1288; G06F 9/451; G06F 1/00; G06F 3/00; G06F 5/00; G06F 7/00; G06F 8/00; G06F 9/00; G06F 11/00; G06F 12/00; G06F 13/00; G06F 15/00; G06F 16/00; G06F 17/00; G06F 18/00; G06Q 30/0201; G06Q 30/0251; G06Q 30/0282; G06Q 20/3226; G06Q 20/327; G06Q 20/343; G06Q 20/352; G06Q 20/401; G06Q 30/0207; G06Q 30/0641; G06Q 10/00; G06Q 20/00; G06Q 30/00; G06Q 40/00; G06Q 50/00; G06Q 90/00; G06Q 99/00; G06Q 2220/00; G06Q 2230/00; G06Q 2240/00; G06Q 2250/00; H04L 67/04; H04L 67/14; H04L 67/141; H04L 67/75; H04L 41/0213; H04L 41/0879; H04L 51/04; H04L 51/216; H04L 51/42; H04L 1/00; H04L 5/00; H04L 7/00; H04L 9/00; H04L 12/00; H04L 13/00; H04L 15/00; H04L 17/00; H04L 19/00; H04L 21/00; H04L 23/00; H04W 4/08; H04W 48/16; H04W 76/10; H04W 4/12; H04W 4/00; H04W 8/00; H04W 12/00; H04W 16/00; H04W 24/00; H04W 28/00; H04W 36/00; H04W 40/00; H04W 48/00; H04W 52/00; G07F 7/0833; G07F 7/084; G07F 9/001; G07F 1/00; G07F 5/00; G07F 7/00; G07F 9/00; G07F 11/00; G07F 15/00; G07F 13/00; G07F 17/00; G07F 19/00; G09B 19/04; G09B 19/06; G09B 5/065; G09B 1/00; G09B 3/00; G09B 5/00; G09B 7/00; G09B 9/00; G09B 11/00; G09B 13/00; G09B 15/00; G09B 17/00; G09B 19/00; G10L 15/26; G10L 17/00; H04M 1/271; H04M 1/72412; H04M 1/72454; H04M 2201/40; H04M 2250/22; H04M 3/5322; H04M 3/53333; H04M 1/00; H04M 3/00; H04M 5/00; H04M 7/00; H04M 9/00; H04M 11/00; H04M 13/00
USPC .... 340/539.13, 539.14, 539.17, 539.22, 566, 340/588, 661, 683, 686.1, 686.6, 691.6, 340/693.3, 825.24, 825.25, 5.61, 5.84, 340/7.6, 286.11
See application file for complete search history.

(56) References Cited

U.S. PATENT DOCUMENTS

| | | | | |
|---|---|---|---|---|
| 2011/0214092 | A1* | 9/2011 | Palmer | G06F 9/451 715/863 |
| 2012/0265535 | A1* | 10/2012 | Bryant-Rich | H04M 1/72433 704/E15.001 |
| 2013/0159784 | A1* | 6/2013 | Rossi | G06F 11/263 714/47.1 |
| 2013/0254002 | A1* | 9/2013 | Isaacson | G06Q 30/0641 705/14.23 |
| 2015/0087264 | A1* | 3/2015 | Goyal | H04W 4/027 455/411 |
| 2018/0329495 | A1* | 11/2018 | Juchem | H04W 88/02 |
| 2021/0335120 | A1 | 10/2021 | Mamishev et al. | |

OTHER PUBLICATIONS

Youhong; The ultimate guide to screenless smart band customization; https://www.jointcorp.com/the-ultimate-guide-to-screenless-smart-band-customization/.

* cited by examiner

200

Screenless Wearable Device 104

Microphone 202

Microcontroller unit (MCU) 204

Transceiver 206

Vibration motor21 208

Sensor Unit 210

Memory 212

Input button 214

Bluetooth Low Energy 216

Battery 218

UPON RECEIVING THE AUDIO ASSOCIATED WITH THE NATURAL SPEECH OF THE ONE OR MORE USERS, GENERATE, BY THE ONE OR MORE COMMUNICATION DEVICES, THE ONE OR MORE REMINDERS BASED ON THE AUDIO ASSOCIATED WITH THE NATURAL SPEECH OF THE ONE OR MORE USERS, USING AN ARTIFICIAL INTELLIGENCE (AI) MODEL

312

DELIVER, BY THE SCREENLESS WEARABLE DEVICE, THE GENERATED ONE OR MORE REMINDERS TO THE ONE OR MORE USERS THROUGH ONE OR MORE HAPTIC VIBRATIONS

314

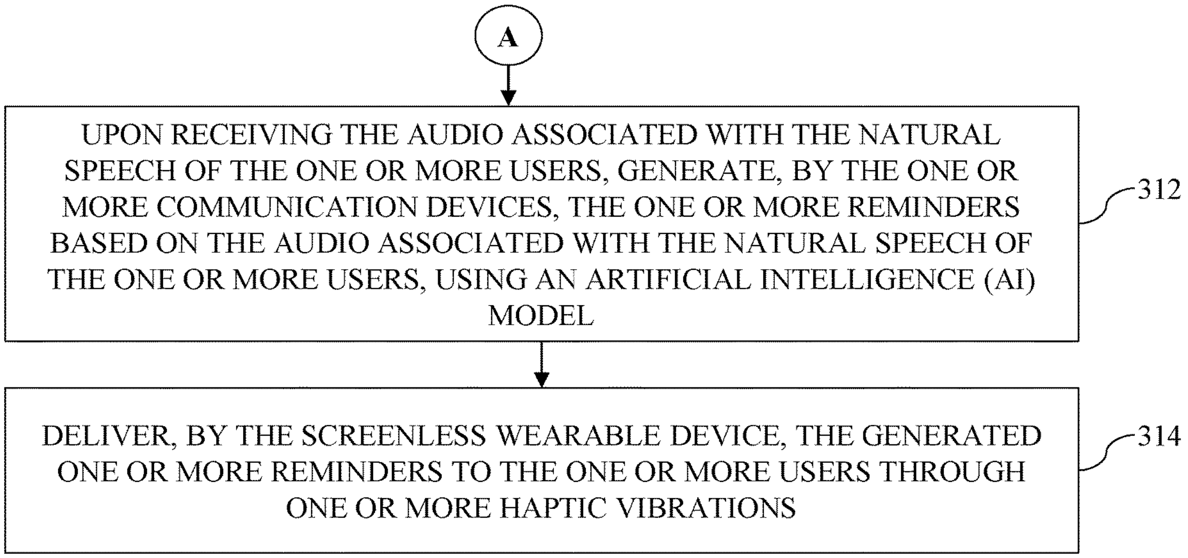

FIG. 3B

COMPUTER-IMPLEMENTED SYSTEM AND METHOD FOR GENERATING REMINDERS FOR USERS USING A SCREENLESS WEARABLE DEVICE

FIELD OF INVENTION

Embodiments of the present disclosure relate to multi-modal data tokenization systems, and more particularly relates to a computer-implemented method and system (i.e., human intention capture and execution system) for generating and delivering one or more reminders for one or more users using a screenless wearable device.

BACKGROUND

In today's fast-paced digital environment, individuals frequently encounter challenges in managing their daily tasks and intentions. Many a times people forget important tasks and intentions due to mental overload and constant digital distractions. The proliferation of smartphones, applications, and digital notifications has created an environment where important tasks are easily overlooked or forgotten amidst the constant stream of information competing for user attention.

Various reminder systems and personal assistant applications have been developed to address the problem of task management and memory assistance. These systems typically rely on smartphone applications, voice-activated assistants, or wearable devices with display screens to help users create, manage, and receive reminders for their daily activities. However, conventional reminder systems suffer from several significant drawbacks that limit their effectiveness and user adoption.

Existing reminder systems require users to manually stop their current work, open an application, and create structured reminders, which often causes intentions to be missed or delayed. This cumbersome process of reminder creation disrupts the natural flow of user activities and requires deliberate effort at the precise moment when a user thinks of a task. By the time a user navigates through multiple steps to create a reminder, the original intention may be forgotten or the urgency diminished.

The problem of notification fatigue caused by frequent alerts, screens, and sounds that compete for attention and are often ignored is a disadvantage in existing system. Users are bombarded with visual and auditory notifications from multiple applications throughout the day, leading to desensitization and a tendency to dismiss or ignore reminders. This notification overload reduces the effectiveness of reminder systems and contributes to the very problem they are designed to solve.

There is a lack of trust in always-listening voice assistants as many existing systems rely on wake words and ambient audio monitoring, which can raise privacy and consent concerns. The users are increasingly wary of devices that continuously monitor their environment for voice commands, as this raises questions about data collection, storage, and potential misuse of personal conversations. This lack of trust creates a barrier to adoption of voice-enabled reminder systems, even when such systems could otherwise provide convenient hands-free operation.

Conventional wearable reminder devices typically incorporate display screens that require visual attention from the user. This screen dependency creates additional distractions and contributes to the digital fatigue experienced by users. Furthermore, screen-based notifications may be inappropriate or disruptive in certain social or professional contexts where visual attention to a device is undesirable.

Hence, there is a need for an improved computer-implemented system and method for generating and delivering one or more reminders for one or more users using a screenless wearable device, in order to address the aforementioned issues.

SUMMARY

This summary is provided to introduce a selection of concepts, in a simple manner, which is further described in the detailed description of the disclosure. This summary is neither intended to identify key or essential inventive concepts of the subject matter nor to determine the scope of the disclosure.

In accordance with an embodiment of the present disclosure, a computer-implemented method for generating one or more reminders for one or more users using a screenless wearable device of the one or more users, is disclosed. The computer-implemented method comprises obtaining, by a transceiver of the screenless wearable device, one or more inputs from the one or more users through an input button.

The computer-implemented method further comprises activating, by a microcontroller unit (MCU) of the screenless wearable device, a microphone to execute a press-to-listen interaction in response to a user providing the one or more inputs through the input button. The microphone is active only for a pre-defined time duration upon receiving the one or more inputs. The computer-implemented method further comprises capturing, by the microphone of the screenless wearable device, natural speech of the one or more users during the pre-defined time duration. The computer-implemented method further comprises analyzing, by the MCU of the screenless wearable device, at least one of: one or more pre-defined code words and one or more phrases related to the one or more reminders from the captured natural speech.

The computer-implemented method further comprises transmitting, by a transceiver of the screenless wearable device, an audio associated with the natural speech of the one or more users to one or more communication devices associated with the one or more users through one or more communication technologies, for processing the audio. The computer-implemented method further comprises upon receiving the audio associated with the natural speech of the one or more users, generating, by the one or more communication devices, the one or more reminders based on the audio associated with the natural speech of the one or more users, using an artificial intelligence (AI) model. The computer-implemented method further comprises delivering, by the screenless wearable device, the generated one or more reminders to the one or more users through one or more haptic vibrations.

In an embodiment, the computer-implemented method further comprising automatically assigning, by the MCU of the screenless wearable device, one or more locations to the one or more reminders based on at least one of: one or more current locations, one or more frequent places, and one or more historical behaviors when the one or more users speak about the one or more reminders without explicitly naming the one or more locations.

In another embodiment, generating, by the one or more communication devices, the one or more reminders based on the audio, comprises: (a) converting, by the one or more communication devices, the audio associated with the natural speech of the one or more users, to one or more texts using automatic speech recognition (ASR) models for downstream text based AI analysis; (b) detecting, by the one or more communication devices, at least one of: one or more specific pre-defined code words from the converted one or more texts, using a trained lightweight AI model; (c) analyzing, by the one or more communication devices, the converted one or more texts to determine one or more user intents differentiating a casual statement and an actionable reminder request using one or more machine learning (ML) classifiers; (d) extracting, by the one or more communication devices, one or more named entities comprising at least one of: one or more items, people, one or more locations, and one or more time references, from the converted one or more texts, using named entity recognition (NER); (e) generating, by the one or more communication devices, the one or more reminders by associating the extracted one or more named entities with the determined one or more user intents; and (f) generating, by the one or more communication devices, reminder metadata comprising at least one of: one or more reminder contents, assigned one or more locations, one or more trigger conditions, urgency level, and one or more sharing permissions.

In yet another embodiment, upon generating the one or more reminders, the computer-implemented method further comprising (a) receiving, by the screenless wearable device, the reminder metadata from the one or more communication devices through the one or more communication technologies; (b) storing, by the MCU of the screenless wearable device, the reminder metadata in an embedded flash memory, wherein the embedded flash memory is configured to store basic system data comprising at least one of: device state, the reminder metadata, and one or more vibration patterns; (c) continuously monitoring, by the screenless wearable device, one or more contextual parameters comprising at least one of: combination of a current location of the one or more users, time, movement status, and routine patterns, to determine whether the one or more trigger conditions associated with the one or more reminders are satisfied, wherein the combination of current location of the one or more users comprise at least one of: when the one or more users enter the one or more locations, when the one or more users exits the one or more locations, when the one or more users are on one or more routes towards the one or more locations, and when the one or more users stay at the one or more locations within a time-window; (d) determining, by a heart rate sensor of the screenless wearable device, a current state of the one or more users, wherein the current state of the one or more users comprises at least one of: busy, stressed, and driving, and wherein the screenless wearable device suppresses the one or more reminders based on the determined current state; and (e) selecting, by the MCU of the screenless wearable device, one or more appropriate vibration patterns from the stored one or more vibration patterns based on at least one of: the urgency level of the one or more reminders and user preferences, wherein one or more vibration patterns indicate at least one of: urgency and follow-up reminders, adapting the one or more users to stay aware without being distracted.

In yet another embodiment, the computer-implemented method further comprising implementing, by the screenless wearable device, privacy-preserving audio lifecycle, by at least one of: (a) buffering, by the screenless wearable device, the natural speech with one or more intent-relevant keywords before transmitting the audio to the one or more communication devices; (b) discarding, by the screenless wearable device, the natural speech with one or more non-relevant keywords before transmitting the audio to the one or more communication devices; and (c) deleting, by the screenless wearable device, data associated with the audio from the screenless wearable device when the audio is transmitted to the one or more communication devices.

In yet another embodiment, the computer-implemented method further comprising at least one of: (a) adapting, by the one or more communication devices, the one or more users to define a time duration for retaining the audio on at least one of: the one or more communication devices and a cloud, based on a user-configurable audio retention policy; (b) adapting, by the one or more communication devices, the one or more users to share the one or more reminders with one or more second users while maintaining one or more private reminders restricted; (c) adapting, by the one or more communication devices, a selective routing of the one or more reminders to one or more defined groups, wherein the one or more defined groups comprise at least one of: one or more family groups and one or more trusted groups; and (d) adapting, by the one or more communication devices, one or more reminder permissions based on one or more roles of the one or more users.

In yet another embodiment, the computer-implemented method further comprising at least one of: (a) identifying, by the one or more communication devices, one or more intended recipients from the captured natural speech at the time of capturing the one or more reminders; and (b) directing, by the one or more communication devices, the one or more reminders to the identified one or more intended recipients.

In yet another embodiment, delivering the one or more reminders through the one or more haptic vibrations comprises at least one of: (a) generating, by the screenless wearable device, a stronger vibration only when the one or more reminders require increased user attention based on at least one of: the urgency level, user responsiveness, and contextual importance; and (b) generating, by the screenless wearable device, a single vibration for each of the one or more reminders unless the one or more reminders are explicitly escalated.

In yet another embodiment, delivering the one or more reminders comprises at least one of: (a) triggering, by the screenless wearable device, the one or more reminders when a confidence threshold associated with the one or more contextual parameters is met; and (b) intentionally delaying, by the screenless wearable device, the triggering of the one or more reminders until the one or more contextual parameters indicate an optimal context for delivery.

In yet another embodiment, the computer-implemented method further comprising at least one of: (a) determining, by the screenless wearable device, an optimal location for the one or more reminders based on one or more historical patterns of the one or more users; (b) triggering, by the screenless wearable device, the one or more reminders when a location condition associated with the determined optimal location is satisfied, and (c) delivering, by the screenless wearable device, the one or more reminders comprising context-aware reminders based on the one or more contextual parameters associated with the one or more users, comprising at least one of: the location, time, movement status, physiological state, environmental conditions, and user behavior.

In yet another embodiment, the computer-implemented method further comprising at least one of: (a) triggering, by the screenless wearable device, the one or more reminders at a next logical time when the one or more locations associated with the one or more reminders are missed by the one or more users; (b) suggesting, by the one or more communication devices, one or more reminder behaviors to the one or more users based on past compliance of the one or more users with previously delivered reminders; and (c) generating, by the one or more communication devices, one or more gentle reminders tied to one or more recovery patterns of the one or more users.

In yet another embodiment, the computer-implemented method further comprising at least one of: (a) monitoring, by the heart rate sensor of the screenless wearable device, one or more health parameters of the one or more users; and (b) reviewing, by the one or more communication devices, at least one of: user activity, heart rate trend, and completed reminders, to suggest one or more recommendations to the one or more users for reaching one or more health goals.

the computer-implemented method further comprising at least one of: (a) discarding the audio, requesting a repeat capture of the audio, generating a tentative reminder for user confirmation through a companion application, and storing the one or more inputs temporarily for deferred reprocessing, when the audio is incomplete, unclear, noisy, and associated with an audio confidence score below a pre-defined threshold; (b) temporarily buffering the audio and extracted intent tokens, deferring reminder generation until connectivity is restored, performing at least partial local processing on at least one of: the screenless wearable device and the one or more communication devices, generating a provisional reminder based on locally available code-word recognition, when an absence of an internet in the one or more communication devices; (c) storing the audio and compressed reminder-relevant data in local memory, retrying transmission upon re-establishment of the one or more communication devices, triggering a local fallback indication to the one or more users, and queuing reminder metadata for later synchronization, when a communication link between the screenless wearable device and the one or more communication devices is interrupted; and (d) assigning a lower confidence state to the generated one or more reminders, routing the one or more reminders to a review queue within the companion application, requesting an optional user confirmation, re-ranking multiple candidate intents, and applying historical user behavior and contextual metadata to refine interpretation, when a wrong intent is detected.

In one aspect, a computer-implemented system for generating one or more reminders for one or more users using a screenless wearable device of the one or more users, is disclosed. The computer-implemented system includes the screenless wearable device configured to: (a) obtain, by a transceiver of the screenless wearable device, one or more inputs from the one or more users through an input button; (b) activate, by a microcontroller unit (MCU) of the screenless wearable device, a microphone to execute a press-to-listen interaction in response to a user providing the one or more inputs through the input button, wherein the microphone is active only for a pre-defined time duration upon receiving the one or more inputs; (c) capture, by the microphone of the screenless wearable device, natural speech of the one or more users during the pre-defined time duration; (d) analyze, by the MCU of the screenless wearable device, at least one of: one or more pre-defined code words and one or more phrases related to the one or more reminders from the captured natural speech; and (e) transmit, by a transceiver of the screenless wearable device, an audio associated with the natural speech of the one or more users to one or more communication devices associated with the one or more users through one or more communication technologies, for processing the audio.

The computer-implemented system further includes the one or more communication devices configured to generate the one or more reminders based on the audio associated with the natural speech of the one or more users, upon receiving the audio associated with the natural speech of the one or more users, using an artificial intelligence (AI) model. The screenless wearable device is further configured to deliver the generated one or more reminders to the one or more users through one or more haptic vibrations.

In another aspect, a non-transitory computer-readable storage medium having instructions stored therein that, when executed by a hardware processor, causes the processor to perform method steps as described above.

To further clarify the advantages and features of the present disclosure, a more particular description of the disclosure will follow by reference to specific embodiments thereof, which are illustrated in the appended figures. It is to be appreciated that these figures depict only typical embodiments of the disclosure and are therefore not to be considered limiting in scope. The disclosure will be described and explained with additional specificity and detail with the appended figures.

BRIEF DESCRIPTION OF DRAWINGS

The disclosure will be described and explained with additional specificity and detail with the accompanying figures in which:

FIG. 3A-3B is a flow chart illustrating a computer-implemented method for generating the one or more reminders for the one or more users using the screenless wearable device of the one or more users, in accordance with another embodiment of the present disclosure.

Figure 1:
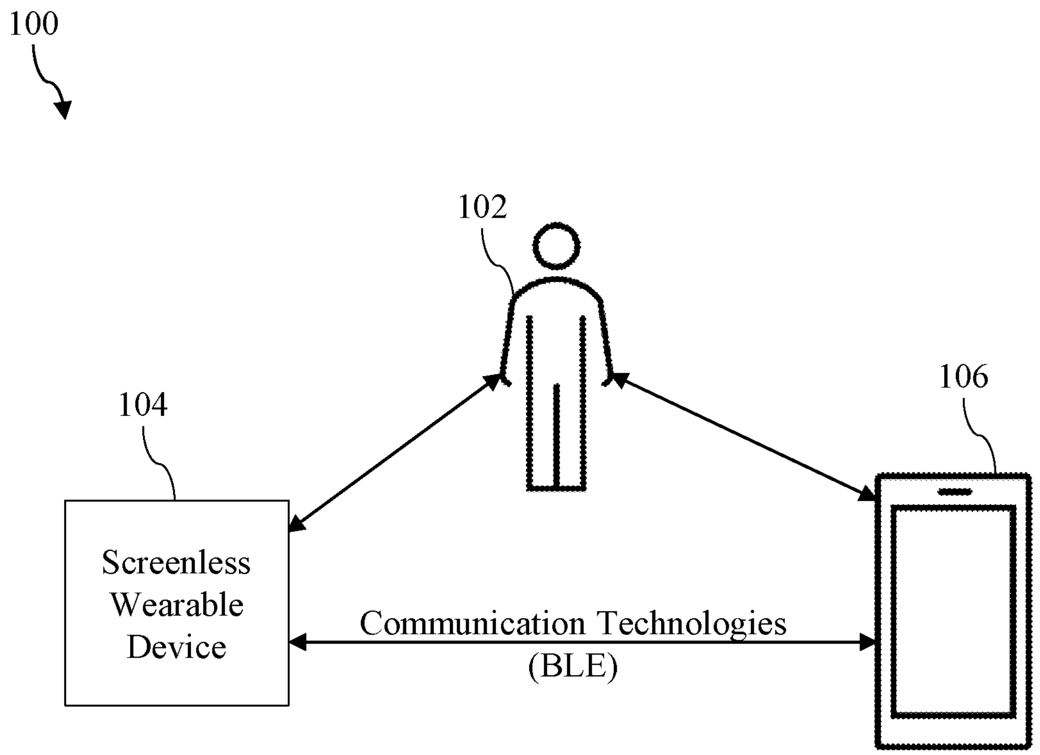
FIG. 1 is a schematic diagram illustrating a computer-implemented system for generating one or more reminders for one or more users using a screenless wearable device of the one or more users, in accordance with an embodiment of the present disclosure.

Further, those skilled in the art will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those skilled in the art having the benefit of the description herein.

DETAILED DESCRIPTION OF THE DISCLOSURE

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications in the illustrated system, and such further applications of the principles of the disclosure as would normally occur to those skilled in the art are to be construed as being within the scope of the present disclosure. It will be understood by those skilled in the art that the foregoing general description and the following detailed description are exemplary and explanatory of the disclosure and are not intended to be restrictive thereof.

In the present document, the word “exemplary” is used herein to mean “serving as an example, instance, or illustration.” Any embodiment or implementation of the present subject matter described herein as “exemplary” is not necessarily to be construed as preferred or advantageous over other embodiments.

The terms “comprise”, “comprising”, or any other variations thereof, are intended to cover a non-exclusive inclusion, such that one or more devices or sub-systems or elements or structures or components preceded by “comprises . . . a” does not, without more constraints, preclude the existence of other devices, sub-systems, additional submodules. Appearances of the phrase “in an embodiment”, “in another embodiment” and similar language throughout this specification may, but not necessarily do, all refer to the same embodiment.

Unless otherwise defined, all technical and scientific terms used herein have the same meaning as commonly understood by those skilled in the art to which this disclosure belongs. The system, methods, and examples provided herein are only illustrative and not intended to be limiting.

A computer system (standalone, client or server computer system) configured by an application may constitute a “module” (or “subsystem”) that is configured and operated to perform certain operations. In one embodiment, the “module” or “subsystem” may be implemented mechanically or electronically, so a module includes dedicated circuitry or logic that is permanently configured (within a special-purpose processor) to perform certain operations. In another embodiment, a “module” or “subsystem” may also comprise programmable logic or circuitry (as encompassed within a general-purpose processor or other programmable processor) that is temporarily configured by software to perform certain operations.

Accordingly, the term “module” or “subsystem” should be understood to encompass a tangible entity, be that an entity that is physically constructed, permanently configured (hardwired) or temporarily configured (programmed) to operate in a certain manner and/or to perform certain operations described herein.

Referring now to the drawings, and more particularly to FIG. 1 through FIG. 3B, where similar reference characters denote corresponding features consistently throughout the figures, there are shown preferred embodiments and these embodiments are described in the context of the following exemplary system and/or method.

FIG. 1 is a schematic diagram illustrating a computer-implemented system 100 (i.e., human intention capture and execution system) for generating one or more reminders for one or more users 102 using a screenless wearable device 104 of the one or more users 102, in accordance with an embodiment of the present disclosure. According to FIG. 1, the computer-implemented system 100 includes one or more communication devices 106 that are communicatively coupled to the screenless wearable device 104. The one or more communication devices 106 through which one or more reminders are generated and delivered to the screenless wearable device 104.

The present invention with the computer-implemented system 100 is configured for generating and delivering the one or more reminders for the one or more users 102 using the screenless wearable device 104 of the one or more users 102. The computer-implemented system 100 includes the screenless wearable device 104 (using a microcontroller unit (MCU)) that is initially configured to obtain one or more inputs from the one or more users 102 through an input button of the screenless wearable device 104. The screenless wearable device 104 is further configured to activate a microphone using the MCU, to execute a press-to-listen interaction in response to the one or more users 102 providing the one or more inputs through the input button. In an embodiment, the microphone is active only for a pre-defined time duration upon receiving the one or more inputs. The press-to-listen interaction refers to a user interaction paradigm in which activation of an audio capture function through the microphone is initiated in response to a discrete user input action, including pressing a physical input button, such that the screenless wearable device 104 listens for user speech/audio only during a defined activation period following the user input.

The screenless wearable device 104 is further configured to capture natural speech of the one or more users 102 during the pre-defined time duration using the microphone of the screenless wearable device 104. In an embodiment, capturing of the natural speech/audio of the one or more users 102 may be non-continuous audio capture (i.e., capturing the privacy audio). In other words, the computer-implemented system 100 is configured to operate without continuous listening, wherein audio capture is activated only upon explicit user input for a predefined duration, thereby preventing passive or background recording of user conversations. The screenless wearable device 104 is further configured to analyze at least one of: one or more pre-defined code words and one or more phrases related to the one or more reminders from the captured natural speech, using the MCU of the screenless wearable device 104. The screenless wearable device 104 with a transceiver is further configured to transmit an audio associated with the natural speech of the one or more users 102 to one or more communication devices 106 associated with the one or more users 102 through one or more communication technologies, for processing the audio. The computer-implemented system 100 supports a local-first processing option, wherein at least a portion of the audio analysis, intent detection, or reminder generation is performed on a local device (i.e., the one or more communication devices 106) associated with the one or more users 102, thereby minimizing reliance on remote servers and enhancing data privacy.

Upon receiving the audio associated with the natural speech of the one or more users 102, the one or more communication devices 106 are initially configured to generate the one or more reminders based on the audio associated with the natural speech of the one or more users 102, using an artificial intelligence (AI) model. The screenless wearable device 104 are further configured to deliver the generated one or more reminders to the one or more users 102 through one or more haptic vibrations. In an embodiment, the computer-implemented system 100 provides user-controlled data retention, allowing the one or more users 102 to define policies governing storage duration, sharing permissions, and deletion of audio or reminder-related data across devices or cloud environments.

In an embodiment, the one or more communication devices 106 may include at least one of: a laptop computer, a desktop computer, a tablet computer, a Smartphone, a wearable device, a Smart watch, and the like. The computer-implemented system 100 may comprise a combination of discrete components, an integrated circuit, an application-specific integrated circuit, a field-programmable gate array, a digital signal processor, or other suitable hardware. The “software” may comprise one or more objects, agents, threads, lines of code, subroutines, separate software applications, two or more lines of code, or other suitable software structures operating in one or more software applications or one or more hardware processors.

In an exemplary embodiment, the screenless wearable device 104 may include a microcontroller unit (shown in FIG. 2), for example, microprocessors, microcomputers, microcontrollers, digital signal processors, hardware processors, central processing units, state machines, logic circuits, and/or any devices that manipulate data or signals based on operational instructions. Among other capabilities, the microcontroller unit may fetch and execute computer-readable instructions in a memory unit operationally coupled with the computer-implemented system 100 for performing tasks such as inputs obtaining, input/output processing, and/or any other functions. Any reference to a task in the present disclosure may refer to an operation being or that may be performed on data. The microcontroller unit is high-performance processors capable of handling large volumes of data and complex computations. The microcontroller unit may be, but not limited to, at least one of: multi-core central processing units (CPU), graphics processing units (GPUs), and the like that enhance an ability of the computer-implemented system 100 to process real-time data from one or more sources simultaneously.

Further, the screenless wearable device 104 may include the memory configured to store all the inputs and results associated with the one or more reminders. In an exemplary embodiment, the computer-implemented system 100 may be implemented by way of a single device or a combination of multiple devices that may be operatively connected or networked together. The computer-implemented system 100 may be implemented in hardware or a suitable combination of hardware and software.

Though few components are disclosed in FIG. 1, there may be additional components and subsystems which is not shown, such as, but not limited to, ports, routers, repeaters, firewall devices, network devices, the one or more databases, network attached storage devices, assets, machinery, instruments, facility equipment, emergency management devices, image capturing devices, any other devices, and combination thereof. The person skilled in the art should not be limiting the components/subsystems shown in FIG. 1. Although FIG. 1 illustrates the computer-implemented system 100, and the one or more communication devices 106 connected to the screenless wearable device 104, one skilled in the art can envision that the computer-implemented system 100, and the one or more communication devices 106 may be connected to several user devices located at various locations and several databases via the one or more communication networks/technologies.

Those of ordinary skilled in the art will appreciate that the hardware depicted in FIG. 1 may vary for particular implementations. For example, other peripheral devices such as an optical disk drive and the like, the local area network (LAN), the wide area network (WAN), wireless (e.g., wireless-fidelity (Wi-Fi)) adapter, graphics adapter, disk controller, input/output (I/O) adapter also may be used in addition or place of the hardware depicted. The depicted example is provided for explanation only and is not meant to imply architectural limitations concerning the present disclosure.

Those skilled in the art will recognize that, for simplicity and clarity, the full structure and operation of all data processing systems suitable for use with the present disclosure are not being depicted or described herein. Instead, only so much of the computer-implemented system 100 as is unique to the present disclosure or necessary for an understanding of the present disclosure is depicted and described. The remainder of the construction and operation of the computer-implemented system 100 may conform to any of the various current implementations and practices that were known in the art.

Figure 2:
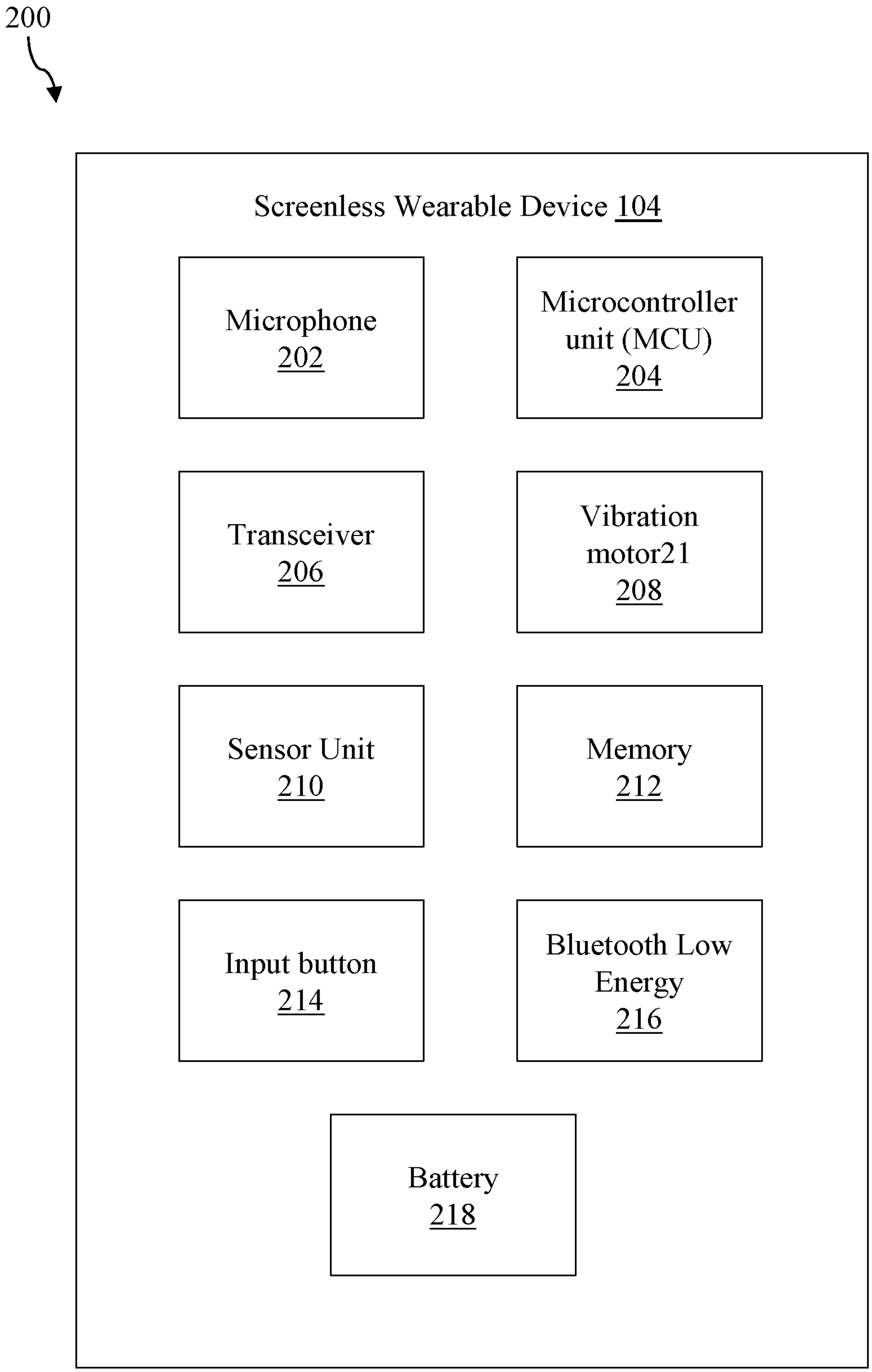
FIG. 2 is a detailed view of the screenless wearable device for generating the one or more reminders for the one or more users, in accordance with another embodiment of the present disclosure.

FIG. 2 is a detailed view 200 of the screenless wearable device 104 for generating the one or more reminders for the one or more users, in accordance with another embodiment of the present disclosure.

In an exemplary embodiment, the screenless wearable device 104 includes the microphone 202, the microcontroller unit (MCU) 204, the transceiver 206, a vibration motor 208, a sensor unit 210, a memory 212 (otherwise referred as memory unit 212), an input button 214, a Bluetooth Low Energy (BLE) 216, and a battery (e.g., rechargeable lithium-polymer battery with wireless charging) 218.

In an exemplary embodiment, the memory unit 212 is operatively connected to the microcontroller unit 204. The memory unit 212 comprises programmable instructions executable by the microcontroller unit 204. The microcontroller unit 204 means any type of computational circuit, such as, but not limited to, the microprocessor unit, microcontroller, complex instruction set computing microprocessor unit, reduced instruction set computing microprocessor unit, very long instruction word microprocessor unit, explicitly parallel instruction computing microprocessor unit, graphics processing unit, digital signal processing unit, or any other type of processing circuit. The microcontroller unit 204 may also include embedded controllers, such as generic or programmable logic devices or arrays, application-specific integrated circuits, single-chip computers, and the like.

The memory unit 212 may be the non-transitory volatile memory and the non-volatile memory. The memory unit 212 may be coupled to communicate with the microcontroller unit 204, such as being a computer-readable storage medium. The microcontroller unit 204 may execute machine-readable instructions and/or source code stored in the memory unit 212. A variety of machine-readable instructions may be stored in and accessed from the memory unit 212. The memory unit 212 may include any suitable elements for storing data and machine-readable instructions, such as read-only memory, random access memory, erasable programmable read-only memory, electrically erasable programmable read-only memory, a hard drive, a removable media drive for handling compact disks, digital video disks, diskettes, magnetic tape cartridges, memory cards, and the like. In the present embodiment, the memory unit 212 includes the machine-readable instructions on any of the above-mentioned storage media and may be in communication with and executed by the microcontroller unit 204.

The screenless wearable device 104 includes the transceiver 206 that is configured to obtain the one or more inputs from the one or more users 102 through the input button 214. The transceiver 206 of the screenless wearable device 104 obtains one or more inputs from the one or more users 102 through the input button 214. The input button 214 is a physical tactile interface element on the screenless wearable device 104 that allows the one or more users 102 to initiate the reminder capture process through a deliberate press or touch. For example, when a user 102 wants to create a reminder about buying groceries, they press the input button 214 on the screenless wearable device 104, which signals the transceiver 206 to register the input and triggers the microcontroller unit 204 to activate the microphone 202 for capturing the user's spoken intent such as "we are out of milk."

The MCU 204 of the screenless wearable device 104 activates the microphone 202 to execute the press-to-listen interaction in response to the one or more users 102 providing the one or more inputs through the input button 214. The microphone 202 is active only for a pre-defined time duration upon receiving the one or more inputs. The microphone 202 of the screenless wearable device 104 captures the natural speech of the one or more users 102 during the pre-defined time duration. The MCU 204 of the screenless wearable device 104 analyzes/recognizes at least one of: the one or more pre-defined code words and the one or more phrases related to the one or more reminders from the captured natural speech.

The MCU 204 is a compact integrated circuit that serves as the central processing and control unit of the screenless wearable device 104, responsible for coordinating all device operations including sensor activation, data processing, and communication management. When pressed, the MCU 204 briefly activates the microphone 202 to capture a short moment of the natural speech. During this time, Aura (the computer-implemented system 100) can recognize the pre-defined code words or the phrases related to the one or more reminders. The computer-implemented system 100 does not use wake words and does not listen in the background. The embedded flash memory (i.e., the memory 212) is only used to store basic system data such as device state, reminder metadata, and vibration patterns.

For example, when a user 102 presses the input button 214 and says "don't forget to call mom tomorrow," the MCU 204 activates the microphone 202 for a pre-defined duration of five seconds, captures the spoken intent, analyzes the speech for relevant code words such as "don't forget" and "call," and then coordinates the transmission of the audio to the paired communication device 106 for further processing while managing the device state and storing the resulting reminder metadata.

In an embodiment, for implementing privacy-preserving audio lifecycle, the screenless wearable device 104 is configured to buffer the natural speech with one or more intent-relevant keywords before transmitting the audio to the one or more communication devices 106. The screenless wearable device 104 is further configured to discard the natural speech with one or more non-relevant keywords before transmitting the audio to the one or more communication devices 106. The screenless wearable device 104 is further configured to delete data associated with the audio from the screenless wearable device 104 when the audio is transmitted to the one or more communication devices 106.

In an embodiment, when the audio is incomplete, unclear, noisy, and associated with an audio confidence score below a predefined threshold, the computer-implemented system 100 may: (a) discard the audio, (b) request a repeat capture of the audio, (c) generate a tentative reminder for user confirmation through a companion application, and (d) store the one or more inputs temporarily for deferred reprocessing.

In an embodiment, the MCU 204 of the screenless wearable device 104 is further configured to automatically assign one or more locations to the one or more reminders based on at least one of: one or more current locations, one or more frequent places, and one or more historical behaviors when the one or more users 102 speak about the one or more reminders without explicitly naming the one or more locations.

The transceiver 206 of the screenless wearable device 104 transmits the audio associated with the natural speech of the one or more users 102 to the one or more communication devices 106 associated with the one or more users 102 through one or more communication technologies, for processing the audio. The audio transmission is a wireless data transfer process where the transceiver 206 sends the captured audio from the screenless wearable device 104 to a paired communication device 106 such as a smartphone using communication technologies such as Bluetooth Low Energy (BLE) 216. In an embodiment, the audio associated with the natural speech of the one or more users 102 is selectively shared with privacy controls. In an embodiment, when an absence of an internet in the one or more communication devices 106, the computer-implemented system 100 may: (a) temporarily buffer the audio and extracted intent tokens, (b) defer reminder generation until connectivity is restored, (c) perform at least partial local processing on at least one of: the screenless wearable device 104 and the one or more communication devices 106, (d) generate a provisional reminder based on locally available code-word recognition.

The captured audio is sent to the paired phone 106 using BLE 216, processed to create a reminder, and then deleted. In an embodiment, no audio is stored on the screenless wearable device 104. This ensures that the screenless wearable device 104 remains lightweight and power-efficient while offloading the computationally intensive audio processing and reminder generation tasks to the communication device 106. For example, when a user 102 presses the input button 214 and says "we need to pick up the dry cleaning," the transceiver 206 transmits the captured audio to the user's paired smartphone 106 via BLE 216, where the smartphone 106 processes the audio using AI models to extract the intent and generate a location-based reminder for the dry cleaning store. In an embodiment, when a communication link (i.e., the BLE link) between the screenless wearable device 104 and the one or more communication devices 106 is interrupted, the screenless wearable device 104 may: (a) store the audio and compressed reminder-relevant data in local memory, (b) retry transmission upon re-establishment of the one or more communication devices, (c) trigger a local fallback indication to the one or more users, and (d) queue reminder metadata for later synchronization.

In an embodiment, the screenless wearable device 104 is further configured to delete data associated with the audio from the screenless wearable device 104 when the audio is transmitted to the one or more communication devices 106. This automatic deletion ensures that no audio recordings are retained on the screenless wearable device 104 after transmission, thereby enhancing user privacy and minimizing the risk of unauthorized access to sensitive voice data. The captured audio is sent to the paired phone (i.e., communication device 106) using BLE 216, processed to create the reminder, and then deleted. No audio is stored on the screenless wearable device 104. For example, when a user 102 presses the input button 214 and says "remind me to call the bank," the audio is immediately transmitted to the paired smartphone 106 and then permanently deleted from the screenless wearable device 104, leaving no trace of the recorded conversation on the screenless wearable device 104 itself.

Upon receiving the audio associated with the natural speech of the one or more users 102, the one or more communication devices 106 are configured to generate the one or more reminders based on the audio associated with the natural speech of the one or more users 102, using the AI model. The reminder is an automatically generated task or intention notification created by the one or more communication devices 106 when it detects relevant intent from the user's spoken words. The AI model is a trained computational algorithm deployed on the communication device 106 that processes the received audio to understand user intent, extract relevant information, and automatically create structured reminders without requiring manual input from the user 102. For example, when a user 102 presses the button and casually says "we are out of milk" or "don't forget the school form," the captured audio is sent to the user's phone 106 for processing, where the AI model detects the relevant intent from the spoken words and creates a reminder based on that input automatically, after which the audio is used to generate the reminder and then deleted. In an embodiment, when a wrong intent is detected, the computer-implemented system 100 may: (a) assign a lower confidence state to the generated one or more reminders, (b) routing the one or more reminders to a review queue within the companion application, (c) request an optional user confirmation, (d) re-rank multiple candidate intents, and (e) apply historical user behavior and contextual metadata to refine interpretation.

For generating the one or more reminders based on the audio, the one or more communication devices 106 are configured to: (a) convert the audio associated with the natural speech of the one or more users 102, to one or more texts using automatic speech recognition (ASR) models for downstream text based AI analysis; (b) detect at least one of: one or more specific pre-defined code words from the converted one or more texts, using a trained lightweight AI model; (c) analyze the converted one or more texts to determine one or more user intents differentiating a casual statement and an actionable reminder request using one or more machine learning (ML) classifiers; (d) extract one or more named entities comprising at least one of: one or more items, people, one or more locations, and one or more time references, from the converted one or more texts, using named entity recognition (NER); (e) generate the one or more reminders by associating the extracted one or more named entities with the determined one or more user intents; and (f) generate reminder metadata comprising at least one of: one or more reminder contents, assigned one or more locations, one or more trigger conditions, urgency level, and one or more sharing permissions.

The one or more communication devices 106 convert the audio associated with the natural speech of the one or more users 102 to one or more texts using automatic speech recognition (ASR) models for downstream text-based AI analysis. The ASR is a technology that transforms spoken language captured as audio signals into written text, enabling subsequent processing by text-based AI models. For example, when a user 102 says "we need to pickup the dry cleaning tomorrow," the ASR model converts this spoken audio into the text string "we need to pick up the dry cleaning tomorrow" which can then be analyzed by downstream AI components.

The one or more communication devices 106 further detect at least one of: the one or more specific pre-defined code words from the converted one or more texts, using the trained lightweight AI model. The lightweight AI model is a compact, efficient neural network trained to identify specific trigger phrases or keywords that indicate reminder intent without requiring extensive computational resources. For example, when the converted text contains phrases such as "we need to," "don't forget," or "remind me," the lightweight AI model flags these as code words indicating that the user 102 intends to create a reminder.

The one or more communication devices 106 further analyze the converted one or more texts to determine one or more user intents differentiating a casual statement and an actionable reminder request using one or more machine learning (ML) classifiers. The ML classifiers are trained algorithms that categorize text inputs into predefined classes, distinguishing between conversational statements that require action and those that do not. For example, when a user 102 says "we are out of milk," the ML classifier determines that this is an actionable reminder request to buy milk, whereas a statement like "I had milk this morning" would be classified as a casual statement requiring no action.

The one or more communication devices 106 further extract the one or more named entities comprising at least one of: one or more items, people, one or more locations, and one or more time references, from the converted one or more texts, using named entity recognition (NER). The NER is an AI technique that identifies and categorizes key information elements within text into predefined categories such as items, people, places, and times. For example, from the text "remind John to pick up medicine from the pharmacy tomorrow evening," NER extracts "John" as a person, "medicine" as an item, "pharmacy" as a location, and "tomorrow evening" as a time reference.

The one or more communication devices 106 further generate the one or more reminders by associating the extracted one or more named entities with the determined one or more user intents. This process combines the identified intent with the extracted entities to create a structured, actionable reminder that captures what needs to be done, by whom, where, and when. For example, when the system determines an intent to "buy" and extracts entities "milk" (item) and "grocery store" (location), it generates a reminder "Buy milk" associated with the grocery store location.

The one or more communication devices 106 further generate the reminder metadata comprising at least one of: one or more reminder contents, assigned one or more locations, one or more trigger conditions, urgency level, and one or more sharing permissions. The reminder metadata is structured data that defines all attributes necessary for the system to store, manage, and deliver the reminder at the appropriate time and context. For example, for a reminder "Pick up kids from school," the generated metadata includes: reminder content ("Pick up kids"), assigned location (school address), trigger condition (when user 102 is within 500 meters of school or at 3:00 PM), urgency level (high), and sharing permissions (shared with spouse).

In an embodiment, the one or more communication devices 106 are configured to adapt/allow the one or more users 102 to define a time duration for retaining the audio on at least one of: the one or more communication devices 106 and a cloud, based on a user-configurable audio retention policy. In an embodiment, the one or more communication devices 106 are further configured to adapt/allow the one or more users 102 to share the one or more reminders with one or more second users while maintaining one or more private reminders restricted. In an embodiment, the one or more communication devices 106 are further configured to adapt a selective routing of the one or more reminders to one or more defined groups. The one or more defined groups include at least one of: one or more family groups and one or more trusted groups. In an embodiment, the one or more communication devices 106 are further configured to adapt one or more reminder permissions based on one or more roles of the one or more users 102.

The one or more communication devices 106 provide granular control over audio data retention and reminder sharing to address privacy concerns while enabling collaborative task management. The user-configurable audio retention policy allows users 102 to specify how long their voice recordings are stored on the communication device 106 or cloud storage, with options ranging from immediate deletion after processing to extended retention for review purposes. The selective sharing functionality enables users 102 to designate specific reminders as shareable with family members or trusted contacts while keeping sensitive reminders such as medical appointments or financial tasks completely private. The role-based permission system allows different levels of access within defined groups, such as allowing a parent to assign reminders to children while restricting children from modifying parental reminders. For example, a user 102 can configure the system to automatically delete all audio recordings after 24 hours, share grocery-related reminders with their spouse, route school pickup reminders to both parents, and keep work-related reminders visible only to themselves, thereby maintaining privacy while facilitating household coordination.

In an embodiment, the one or more communication devices 106 are further configured to identify one or more intended recipients from the captured natural speech at the time of capturing the one or more reminders. The one or more communication devices 106 are further configured to direct the one or more reminders to the identified one or more intended recipients.

The one or more communication devices 106 may utilize natural language processing to identify the one or more intended recipients from the captured natural speech at the time of capturing the one or more reminders, enabling the system to automatically determine who should receive a particular reminder based on contextual cues in the user's spoken words. When a user 102 speaks a reminder such as "remind John to pick up the kids" or "tell mom to call the doctor," the system extracts the named person as the intended recipient and associates the reminder with that individual. The one or more communication devices 106 then direct the one or more reminders to the identified one or more intended recipients, delivering the reminder only to the target user's screenless wearable device 104 rather than to the person who created the reminder. This recipient-aware delivery ensures that reminders reach the appropriate person without requiring the sender to manually select recipients through an application interface. For example, if a parent says "remind Sarah to finish her homework before dinner," the system identifies "Sarah" as the intended recipient and delivers the reminder directly to Sarah's screenless wearable device 104 at the appropriate time, while the parent receives no notification unless follow-up is needed.

In an embodiment, the one or more reminders are delivered only to the target user's wearable (recipient-aware delivery). In an embodiment, the reminder sender does not receive any notification unless one or more follow-up is needed (i.e., silent degradation). In an embodiment, one or more communication devices 106 are further configured to share the one or more reminders only when the one or more reminders are explicitly marked as shareable (private-by-default reminders). In an embodiment, the recipient completion may notify the sender (i.e., completion acknowledgement).

Upon generating the one or more reminders, the screenless wearable device 104 is further configured to receive the reminder metadata from the one or more communication devices 106 through the one or more communication technologies (e.g., BLE 216). The reminder metadata reception is a wireless data transfer process where the screenless wearable device 104 receives structured reminder information from the paired communication device 106 via the BLE 216 after the reminder has been generated. For example, after the user's phone 106 processes the spoken intent "pick up kids from school at 3 PM," the phone 106 transmits the reminder metadata including the reminder content, school location, trigger time, and urgency level back to the screenless wearable device 104 for local storage and monitoring.

The MCU 204 of the screenless wearable device 104 stores the reminder metadata in an embedded flash memory 212, wherein the embedded flash memory 212 is configured to store basic system data comprising at least one of: device state, the reminder metadata, and one or more vibration patterns. The embedded flash memory 212 is a non-volatile storage component within the screenless wearable device 104 that retains data even when the screenless wearable device 104 is powered off, enabling the screenless wearable device 104 to maintain reminder information and system configurations without requiring continuous connection to the paired phone 106. For example, when the screenless wearable device 104 receives reminder metadata for "buy groceries," the MCU 204 stores this data in the embedded flash memory 212 along with the associated vibration pattern for a routine reminder, allowing the screenless wearable device 104 to trigger the reminder independently even if the phone 106 connection is temporarily lost.

The screenless wearable device 104 continuously monitors the one or more contextual parameters comprising at least one of: combination of a current location of the one or more users 102, time, movement status, and routine patterns, to determine whether the one or more trigger conditions associated with the one or more reminders are satisfied. The combination of current location of the one or more users 102 comprise at least one of: when the one or more users 102 enter the one or more locations, when the one or more users 102 exit the one or more locations, when the one or more users 102 are on one or more routes towards the one or more locations, and when the one or more users 102 stay at the one or more locations within a time-window. The contextual parameter monitoring is an ongoing process where the screenless wearable device 104 tracks multiple environmental and behavioral factors to intelligently determine the optimal moment to deliver a reminder based on predefined trigger conditions. For example, if a user 102 has a reminder to "buy milk," the screenless wearable device 104 monitors the user's location and detects when the user 102 enters a grocery store, is on a route towards the grocery store, or stays near the grocery store for more than two minutes, and triggers the reminder (i.e., the context-aware reminders) accordingly. The context-aware reminders are the one or more reminders configured to be generated, scheduled, modified, or triggered based on one or more contextual parameters associated with the one or more users, including but not limited to location, time, movement status, physiological state, environmental conditions, or user behavior.

The sensor unit 210 comprising the heart rate sensor of the screenless wearable device 104 determines a current state (i.e., physiological state) of the one or more users 102. The current state of the one or more users 102 comprises at least one of: busy, stressed, and driving. The screenless wearable device 104 suppresses the one or more context-aware reminders based on the determined current state. The heart rate sensor (PPG) is a photoplethysmography-based sensor that measures the user's heart rate and heart rate variability to infer the user's physiological and activity state, enabling the screenless wearable device 104 to make intelligent decisions about whether to deliver or suppress reminders based on the user's current condition. For example, if the heart rate sensor detects elevated heart rate patterns consistent with stress or physical activity, or motion patterns indicating the user 102 is driving, the screenless wearable device 104 suppresses a low-priority reminder about picking up dry cleaning and delays delivery until the user's state returns to a calm, receptive condition.

In an embodiment, the heart rate sensor of the screenless wearable device 104 is configured to monitor one or more health parameters of the one or more users 102. The one or more communication devices 106 are configured to review at least one of: user activity, heart rate trend, and completed reminders, to suggest one or more recommendations to the one or more users 102 for reaching one or more health goals.

The heart rate sensor of the screenless wearable device 104 utilizes photoplethysmography (PPG) technology to continuously track the user's heart rate and heart rate variability throughout the day, capturing physiological data that reflects the user's overall wellness state without requiring active user input. The heart rate sensor (PPG) is a photoplethysmography-based sensor that measures the user's heart rate and heart rate variability to infer the user's physiological and activity state. The one or more communication devices 106 aggregate this health data along with reminder completion patterns and daily activity levels to build a comprehensive picture of the user's lifestyle habits and wellness trends over time. By reviewing daily activity and heart rate trends, the system can suggest simple ideas to support health goals, without continuous monitoring or medical claims. This approach provides wellness support as an added benefit rather than a primary function, avoiding the intrusiveness of dedicated health monitoring devices. For example, at the end of the day, the companion app can review the user's completed reminders, activity levels, and heart rate trends to suggest simple recommendations such as "You completed all your tasks today but your activity was low—consider a short walk tomorrow" without making medical diagnoses or requiring constant sensor monitoring.

The MCU 204 of the screenless wearable device 104 selects one or more appropriate vibration patterns from the stored one or more vibration patterns based on at least one of: the urgency level of the one or more reminders and user preferences. The one or more vibration patterns indicate at least one of: urgency and follow-up reminders, adapting the one or more users 102 to stay aware without being distracted. The Vibration pattern selection is a decision-making process where the MCU 204 chooses the most appropriate haptic feedback pattern from a library of stored patterns to communicate the nature and importance of a reminder without requiring the user 102 to look at a screen. For example, when a high-urgency reminder such as "take medication" is triggered, the MCU 204 selects a longer, stronger vibration pattern to capture the user's attention, whereas a routine reminder such as "water the plants" triggers a short, gentle pulse, and if the user 102 does not acknowledge the reminder, a distinct follow-up vibration pattern is selected to indicate a repeated notification.

The screenless wearable device 104 is further configured to deliver the generated one or more reminders to the one or more users 102 through one or more haptic vibrations. The one or more haptic vibrations are tactile feedback signals produced by the vibration motor 208 within the screenless wearable device 104 that alert the one or more users 102 through physical sensation on the skin rather than through visual displays or audible sounds. The one or more reminders are delivered using gentle haptic vibrations instead of screen notifications, and different vibration patterns can represent urgency or follow-up reminders, allowing the one or more users 102 to stay aware without being distracted.

For example, if the user 102 goes near a grocery shop, the screenless wearable device 104 will remind automatically, saying that the user 102 needs to buy milk, and the screenless wearable device 104 delivers this reminder through a gentle vibration on the user's wrist, with a short pulse indicating a routine reminder or a longer, stronger vibration pattern indicating an urgent task.

For delivering the one or more reminders through the one or more haptic vibrations, the screenless wearable device 104 is configured to generate a stronger vibration only when the one or more reminders require increased user attention based on at least one of: the urgency level, user responsiveness, and contextual importance. The screenless wearable device 104 is further configured to generate a single vibration for each of the one or more reminders unless the one or more reminders are explicitly escalated. In an embodiment, the screenless wearable device 104 is further configured to use user's location data to deliver contextually relevant reminders to the one or more users 102.

The screenless wearable device 104 employs an intelligent haptic delivery system that adapts vibration intensity and frequency based on multiple contextual factors to ensure reminders are delivered effectively without causing unnecessary distraction. The screenless wearable device 104 is configured to generate a stronger vibration only when the one or more reminders require increased user attention based on at least one of: the urgency level, user responsiveness, and contextual importance. This adaptive approach ensures that routine reminders such as "water the plants" produce only a gentle pulse, while time-sensitive reminders such as "take medication" generate more pronounced vibrations to capture the user's attention. The screenless wearable device 104 is further configured to generate a single vibration for each of the one or more reminders unless the one or more reminders are explicitly escalated. The screenless wearable device 104 is further configured to use user's location data to deliver contextually relevant reminders to the one or more users 102. The location-aware delivery ensures that reminders are triggered at the most appropriate moment, such as when the user 102 arrives at a grocery store for a shopping-related reminder. This combination of urgency-based vibration intensity, non-repeating haptics, and location-based triggering creates a reminder experience that is both effective and minimally intrusive, allowing users 102 to stay aware of their tasks without being overwhelmed by constant notifications.

For delivering the one or more reminders, the screenless wearable device 104 is configured to trigger the one or more reminders when a confidence threshold associated with the one or more contextual parameters is met. The screenless wearable device 104 is further configured to intentionally delay the triggering of the one or more reminders until the one or more contextual parameters indicate an optimal context for delivery.

The confidence threshold is a predefined minimum score that the system calculates based on the reliability and relevance of multiple contextual factors such as location accuracy, time alignment, and user activity state. By requiring a confidence threshold to be met before triggering, the system avoids delivering reminders based on uncertain or incomplete contextual data, such as when GPS signals are weak or when the user's location is ambiguous. The intentional delay mechanism ensures that reminders are not delivered at inconvenient moments, such as when the user 102 is in a meeting, exercising, or driving, even if other trigger conditions are technically satisfied. The contextual parameter monitoring is an ongoing process where the screenless wearable device 104 tracks multiple environmental and behavioral factors to intelligently determine the optimal moment to deliver a reminder based on predefined trigger conditions. For example, if a user 102 has a reminder to "buy milk," the screenless wearable device 104 monitors the user's location and detects when the user 102 enters a grocery store, is on a route towards the grocery store, or stays near the grocery store for more than two minutes, and triggers the reminder accordingly.

The screenless wearable device 104 is configured to determine an optimal location for the one or more reminders based on one or more historical patterns of the one or more users 102. The screenless wearable device 104 is further configured to trigger the one or more reminders when a location condition associated with the determined optimal location is satisfied. In an embodiment, the screenless wearable device 104 is configured to deliver the one or more reminders (i.e., context-aware reminders) upon determining the optimal location of the one or more users 102 based on one or more physiological states of the one or more users 102.

The historical patterns include data such as frequently visited locations, typical routes taken by the user 102, time-of-day location preferences, and past reminder completion locations that help the system predict where the user 102 is most likely to act on a particular reminder. The optimal location determination process analyzes these patterns to identify the most suitable location for triggering each reminder, even when the user 102 does not explicitly specify a location during reminder creation. For example, if a user 102 frequently buys groceries from a particular store every Saturday afternoon, and the user 102 creates a reminder saying "we need eggs," the screenless wearable device 104 analyzes the historical patterns to determine that the optimal location for this reminder is the user's preferred grocery store, and triggers the reminder when the user 102 approaches or enters that store, rather than triggering at any random grocery store or at an inconvenient time.

The screenless wearable device 104 is configured to trigger the one or more reminders at a next logical time when the one or more locations associated with the one or more reminders are missed by the one or more users 102. This fallback triggering mechanism ensures that important reminders are not permanently lost when a user 102 fails to visit the intended location, instead rescheduling the reminder to the next appropriate opportunity based on the user's schedule and routine patterns.

The one or more communication devices 106 are configured to suggest one or more reminder behaviors to the one or more users 102 based on past compliance of the one or more users 102 with previously delivered reminders. This health-informed suggestion engine analyzes patterns such as which types of reminders the user 102 consistently completes versus ignores, and provides personalized recommendations to improve task completion rates over time.

The one or more communication devices 106 are further configured to generate one or more gentle reminders tied to one or more recovery patterns of the one or more users 102. These passive wellness nudges are non-intrusive notifications that encourage healthy behaviors such as taking breaks, staying hydrated, or resting based on the user's activity levels and physiological data without making medical claims. For example, if a user 102 misses a reminder to pick up groceries because they did not pass by the store, the system triggers the reminder the next morning before the user 102 leaves for work, and if the user 102 has been consistently ignoring exercise-related reminders, the system may suggest setting reminders for shorter walks instead.

In an embodiment, a power management system (i.e., rechargeable lithium-polymer battery 218) and inductive wireless charging allow the screenless wearable device 104 to be worn daily without frequent charging or exposed ports. The companion application for the screenless wearable device 104 is used for setup, reviewing reminders, managing permissions, enabling features like location or health sensing, and controlling optional family sharing and third-party connections.

Figure 3A:
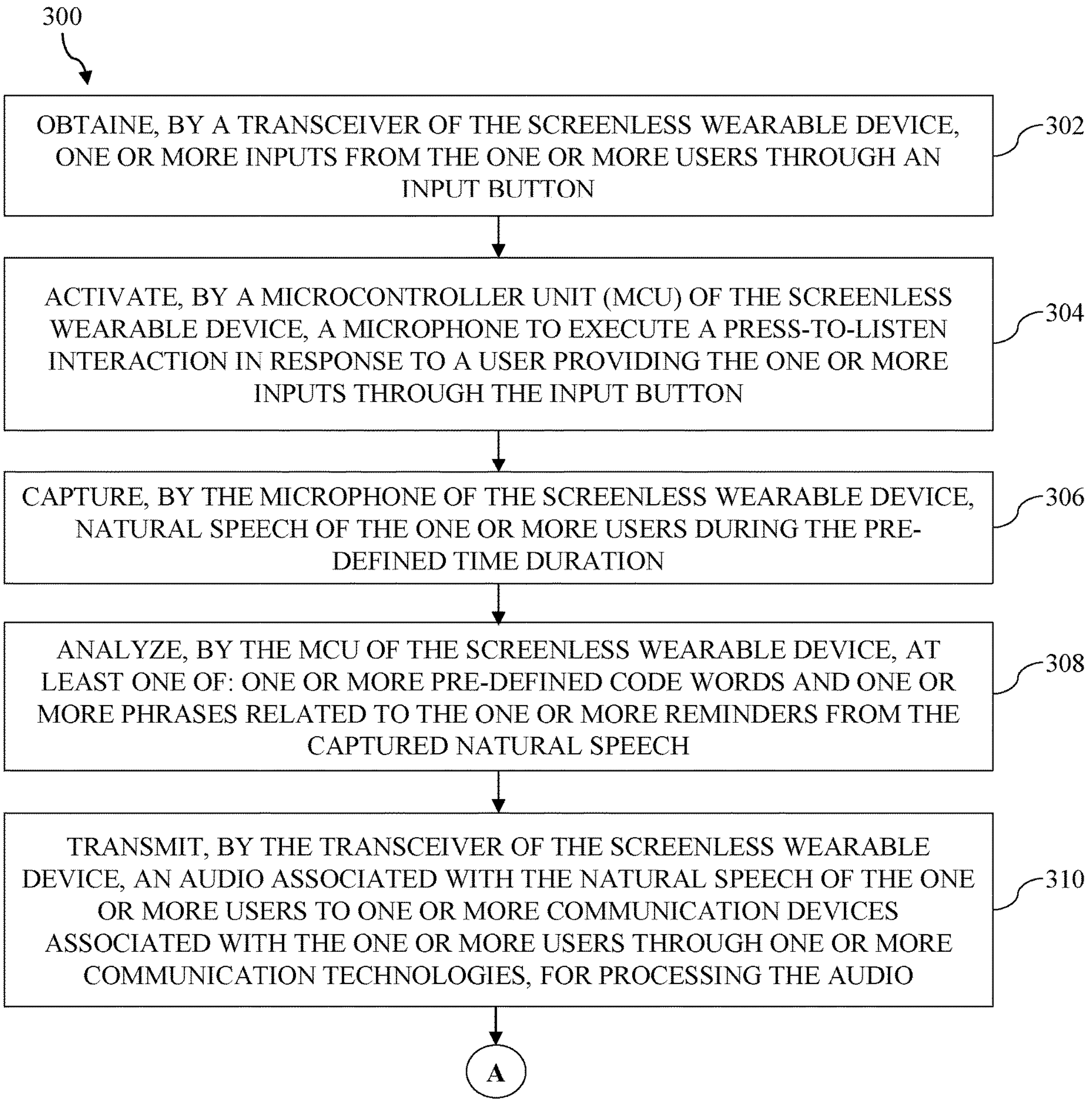

FIG. 3A-3B is a flow chart illustrating a computer-implemented method 300 for generating the one or more reminders for the one or more users 102 using the screenless wearable device 104 of the one or more users 102, in accordance with another embodiment of the present disclosure.

At step 302, the transceiver 206 of the screenless wearable device 104 obtains the one or more inputs are obtained from the one or more users 102 through the input button 214.

At step 304, the microcontroller unit (MCU) 204 of the screenless wearable device 104 activates the microphone 202 to execute the press-to-listen interaction in response to the one or more users 102 providing the one or more inputs through the input button 214. In an embodiment, the microphone 202 is active only for the pre-defined time duration upon receiving the one or more inputs.

At step 306, the microphone 202 of the screenless wearable device 104 captures the natural speech of the one or more users 102 during the pre-defined time duration.

At step 308, the MCU 204 of the screenless wearable device 104 analyzes at least one of: the one or more pre-defined code words and the one or more phrases related to the one or more reminders from the captured natural speech.

At step 310, the transceiver 206 of the screenless wearable device 104 transmits the audio associated with the natural speech of the one or more users 102 to the one or more communication devices 106 associated with the one or more users 102 through the one or more communication technologies, for processing the audio.

At step 312, upon receiving the audio associated with the natural speech of the one or more users 102, the one or more communication devices 106 generate the one or more reminders based on the audio associated with the natural speech of the one or more users 102, using the AI model.

At step 314, the screenless wearable device 104 delivers the generated one or more reminders to the one or more users 102 through the one or more haptic vibrations.

In FIG. 3A-3B, the circular symbol with "A" written inside is being used as an off-page connector. This is used for indicating that FIG. 3A continues to the next page as FIG. 3B.

The one or more use case scenarios based on the computer-implemented system 100 with the screenless wearable device 104, are given below.

Grocery reminder (location-based): A user 102 presses the input button on the screenless wearable device 104 and casually says, "We are out of milk." The computer-implemented system 100 captures the natural speech, extracts the item "milk", infers a grocery-related intent, and automatically assigns a likely grocery store based on current location, frequent shopping locations, or historical behavior. The reminder is then triggered through a haptic vibration when the user 102 is: entering a grocery store, on a route toward the grocery store, or staying near the grocery store within a defined time window.

Parent-to-child reminder (shared reminder): A parent/user 102 presses the wearable input button and says, "Remind Sarah to finish her homework before dinner." The computer-implemented system 100 identifies "Sarah" as the intended recipient, classifies the speech as a reminder request, and routes the generated reminder only to Sarah's associated wearable device. In some embodiments, the reminder remains private-by-default, and the sender is not notified unless follow-up or completion acknowledgement is required. This enables recipient-aware family reminder routing without requiring a shared calendar or direct manual assignment.

Health-aware delay (stress or busy state detected): A user 102 has an existing reminder such as "Pick up dry cleaning." The reminder becomes eligible for delivery based on time or location, but the screenless wearable device 104 determines from heart rate sensor data and/or movement status that the user 102 is currently stressed, busy, or driving. Instead of immediately vibrating, the computer-implemented system 100 suppresses or intentionally delays delivery until a more appropriate and less disruptive context is detected. This supports context-sensitive reminder timing and reduces interruption during physiologically or behaviourally unsuitable states.

Missed reminder→automatically rescheduled: A user 102 creates a reminder such as "Take medication at 8 PM." The computer-implemented system 100 extracts the time reference and classifies the reminder as high urgency. At the trigger time, the screenless wearable device 104 selects a stronger or longer haptic vibration pattern compared to a routine reminder, thereby increasing the probability of user attention without requiring a display or audible alarm. If user responsiveness is low, a follow-up vibration may be used based on configured escalation behavior.

In some aspects, the computer-implemented system 100 with the screenless wearable device 104 may be integrated into at least one of: smart home devices, one or more vehicles, enterprise or workplace usage, healthcare reminder systems, education or student productivity, and the like.

The present invention has the following advantages. The computer-implemented system 100 for generating the one or more reminders for the one or more users 102 using the screenless wearable device 104 of the one or more users 102.

Unlike prior solutions that rely on always-on microphones or wake words, this invention only listens when the user 102 intentionally presses a button. This improves privacy, builds trust, and reduces battery drain compared to devices that are always listening. The button-activated approach ensures that audio capture occurs only during deliberate user interaction, eliminating concerns about ambient monitoring or unauthorized recording of private conversations. For example, when a user 102 is having a confidential discussion at home or in the office, the screenless wearable device 104 remains completely silent and inactive until the user 102 explicitly chooses to capture a reminder by pressing the button 214.

Unlike existing systems such as smartphones, smartwatches, and voice assistants, the present invention with the screenless wearable device 104 is configured to operate without requiring continuous always-on listening, screen-dependent interaction, structured command-based invocation, or excessive notification delivery for user engagement. In an embodiment, the present invention enables interaction through a context-aware and low-friction system architecture that reduces reliance on persistent audio monitoring, visual interface dependency, predefined command syntax, and interruption-heavy notification mechanisms, thereby improving usability, interaction efficiency, and contextual responsiveness.

The present invention allows the one or more users 102 to speak naturally instead of using structured commands. By recognizing code words during short, intentional recordings, the system captures intent in the moment without requiring users 102 to remember special phrases or open an application. This natural language approach reduces cognitive burden on users 102 who would otherwise need to formulate specific command syntax or navigate through application interfaces. For example, instead of saying "Hey device, set a reminder to buy milk at the grocery store," a user 102 can simply press the button and casually say "we are out of milk" during a conversation, and the system automatically detects the intent and creates an appropriate reminder.

The present invention reduces notification overload. Instead of sending frequent alerts or screen-based notifications, reminders are delivered through simple haptic vibrations, which are quieter and less distracting. The Haptic vibrations provide a discreet, non-intrusive method of alerting users 102 that does not compete with other visual or auditory stimuli in the environment. For example, when a user 102 enters a grocery store, the screenless wearable device 104 delivers a gentle vibration to remind them about buying milk, without producing sounds that might disturb others or requiring the user 102 to look at a screen.

The present invention is screenless by default but still gives users 102 clarity when they want it. If a user 102 is unsure what the vibration was for, they can open the companion app to see the exact reminder and what action is needed. This makes it calm most of the time, but detailed when necessary. This hybrid approach balances simplicity with accessibility, allowing the users 102 to remain undistracted during normal operation while providing full information access when needed. For example, if a user 102 receives a haptic vibration but cannot immediately recall the associated task, they can quickly open the companion app on their phone to view the reminder details such as "Pick up dry cleaning" along with the location and any other relevant context.

The present invention offers privacy-first family sharing. Existing solutions often rely on shared calendars, group chats, or tracking. This system allows specific reminders to be shared intentionally, while keeping everything else private by default. This selective sharing model respects individual privacy while enabling collaborative task management within trusted groups. For example, a parent can share a reminder about picking up the children from school with their spouse, while keeping personal reminders such as "call doctor about test results" completely private and invisible to other family members.

The present invention is power-efficient. Because sensing, audio capture, and wireless communication happen only during short moments, the device can last longer between charges and supports wireless charging for easier daily use. The momentary activation design minimizes battery consumption by keeping power-intensive components such as the microphone 202, BLE 216, and transceiver 206 dormant until explicitly needed. For example, a user 102 can wear the device throughout an entire day or multiple days without recharging, and when the battery 218 does need charging, the wireless charging capability allows the user 102 to simply place the device on a charging pad without dealing with cables or exposed charging ports.

The present invention can include optional health insights in a non-invasive way. By reviewing daily activity and heart rate trends, the system can suggest simple ideas to support health goals, without continuous monitoring or medical claims. This approach provides wellness support as an added benefit rather than a primary function, avoiding the intrusiveness of dedicated health monitoring devices. For example, at the end of the day, the companion app can review the user's completed reminders, activity levels, and heart rate trends to suggest simple recommendations such as "You completed all your tasks today but your activity was low—consider a short walk tomorrow" without making medical diagnoses or requiring constant sensor monitoring.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer-readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD.

Input/output (I/O) devices (including but not limited to keyboards, displays, pointing devices, etc.) can be coupled to the computer-implemented system 100 either directly or through intervening I/O controllers. Network adapters may also be coupled to the computer-implemented system 100 to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments may include a hardware configuration of an information handling/computer-implemented system 100 in accordance with the embodiments herein, the computer-implemented system 100 herein comprises at least one processor or central processing unit (CPU). The CPUs are interconnected via the system bus to various devices including at least one of: a random-access memory (RAM), read-only memory (ROM), and an input/output (I/O) adapter. The I/O adapter can connect to peripheral devices, including at least one of: disk units and tape drives, or other program storage devices that are readable by the computer-implemented system 100. The computer-implemented system 100 can read the inventive instructions on the program storage devices and follow these instructions to execute the methodology of the embodiments herein.

The computer-implemented system 100 further includes a user interface adapter that connects a keyboard, mouse, speaker, microphone, and/or other user interface devices including a touch screen device (not shown) to the bus to gather user input. Additionally, a communication adapter connects the bus to a data processing network, and a display adapter connects the bus to a display device which may be embodied as an output device including at least one of: a monitor, printer, or transmitter, for example.

A description of an embodiment with several components in communication with each other does not imply that all such components are required. On the contrary, a variety of optional components are described to illustrate the wide variety of possible embodiments of the invention. When a single device or article is described herein, it will be apparent that more than one device/article (whether or not they cooperate) may be used in place of a single device/article. Similarly, where more than one device or article is described herein (whether or not they cooperate), it will be apparent that a single device/article may be used in place of the more than one device or article, or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open-ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that are issued on an application based here on. Accordingly, the embodiments of the present invention are intended to be illustrative, but not limiting, of the scope of the invention, which is set forth in the following claims.

What is claimed is:

1. A computer-implemented method for generating one or more reminders for one or more users using a screenless wearable device of the one or more users, the computer-implemented method comprising:

obtaining, by a transceiver of the screenless wearable device, one or more inputs from the one or more users through an input button;

activating, by a microcontroller unit (MCU) of the screenless wearable device, a microphone to execute a press-to-listen interaction in response to the one or more users providing the one or more inputs through the input button, wherein the microphone is active only for a pre-defined time duration upon receiving the one or more inputs;

capturing, by the microphone of the screenless wearable device, natural speech of the one or more users during the pre-defined time duration;

analyzing, by the MCU of the screenless wearable device, at least one of: one or more pre-defined code words and one or more phrases related to the one or more reminders from the captured natural speech;

transmitting, by the transceiver of the screenless wearable device, an audio associated with the natural speech of the one or more users to one or more communication devices associated with the one or more users through one or more communication technologies, for processing the audio;

upon receiving the audio associated with the natural speech of the one or more users, generating, by the one or more communication devices, the one or more reminders based on the audio associated with the natural speech of the one or more users, using an artificial intelligence (AI) model; and delivering, by the screenless wearable device, the generated one or more reminders to the one or more users through one or more haptic vibrations.

2. The computer-implemented method of claim 1, further comprising automatically assigning, by the MCU of the screenless wearable device, one or more locations to the one or more reminders based on at least one of: one or more current locations, one or more frequent places, and one or more historical behaviors when the one or more users speak about the one or more reminders without explicitly naming the one or more locations.

3. The computer-implemented method of claim 1, wherein generating, by the one or more communication devices, the one or more reminders based on the audio, comprises:

converting, by the one or more communication devices, the audio associated with the natural speech of the one or more users, to one or more texts using automatic speech recognition (ASR) models for downstream text based AI analysis;

detecting, by the one or more communication devices, at least one of: one or more specific pre-defined code words from the converted one or more texts, using a trained lightweight AI model;

analyzing, by the one or more communication devices, the converted one or more texts to determine one or more user intents differentiating a casual statement and an actionable reminder request using one or more machine learning (ML) classifiers;

extracting, by the one or more communication devices, one or more named entities comprising at least one of: one or more items, people, one or more locations, and one or more time references, from the converted one or more texts, using named entity recognition (NER);

generating, by the one or more communication devices, the one or more reminders by associating the extracted one or more named entities with the determined one or more user intents; and generating, by the one or more communication devices, reminder metadata comprising at least one of: one or more reminder contents, assigned one or more locations, one or more trigger conditions, urgency level, and one or more sharing permissions.

4. The computer-implemented method of claim 1, upon generating the one or more reminders, further comprising:

receiving, by the screenless wearable device, the reminder metadata from the one or more communication devices through the one or more communication technologies;

storing, by the MCU of the screenless wearable device, the reminder metadata in an embedded flash memory, wherein the embedded flash memory is configured to store basic system data comprising at least one of: device state, the reminder metadata, and one or more vibration patterns;

continuously monitoring, by the screenless wearable device, one or more contextual parameters comprising at least one of: combination of a current location of the one or more users, time, movement status, and routine patterns, to determine whether the one or more trigger conditions associated with the one or more reminders are satisfied, wherein the combination of current location of the one or more users comprise at least one of: when the one or more users enter the one or more locations, when the one or more users exits the one or more locations, when the one or more users are on one or more routes towards the one or more locations, and when the one or more users stay at the one or more locations within a time-window;

determining, by a heart rate sensor of the screenless wearable device, a current state of the one or more users, wherein the current state of the one or more users comprises at least one of: busy, stressed, and driving, and wherein the screenless wearable device suppresses the one or more reminders based on the determined current state; and selecting, by the MCU of the screenless wearable device, one or more appropriate vibration patterns from the stored one or more vibration patterns based on at least one of: the urgency level of the one or more reminders and user preferences, wherein one or more vibration patterns indicate at least one of: urgency and follow-up reminders, adapting the one or more users to stay aware without being distracted.

5. The computer-implemented method of claim 1, further comprising implementing, by the screenless wearable device, privacy-preserving audio lifecycle, by at least one of:

buffering, by the screenless wearable device, the natural speech with one or more intent-relevant keywords before transmitting the audio to the one or more communication devices;

discarding, by the screenless wearable device, the natural speech with one or more non-relevant keywords before transmitting the audio to the one or more communication devices; and deleting, by the screenless wearable device, data associated with the audio from the screenless wearable device when the audio is transmitted to the one or more communication devices.

6. The computer-implemented method of claim 1, further comprising at least one of:

adapting, by the one or more communication devices, the one or more users to define a time duration for retaining the audio on at least one of: the one or more communication devices and a cloud, based on a user-configurable audio retention policy;

adapting, by the one or more communication devices, the one or more users to share the one or more reminders with one or more second users while maintaining one or more private reminders restricted;

adapting, by the one or more communication devices, a selective routing of the one or more reminders to one or more defined groups, wherein the one or more defined groups comprise at least one of: one or more family groups and one or more trusted groups; and adapting, by the one or more communication devices, one or more reminder permissions based on one or more roles of the one or more users.

7. The computer-implemented method of claim 1, further comprising at least one of:

identifying, by the one or more communication devices, one or more intended recipients from the captured natural speech at the time of capturing the one or more reminders; and directing, by the one or more communication devices, the one or more reminders to the identified one or more intended recipients.

8. The computer-implemented method of claim 1, wherein delivering the one or more reminders through the one or more haptic vibrations comprises at least one of:

generating, by the screenless wearable device, a stronger vibration only when the one or more reminders require increased user attention based on at least one of: the urgency level, user responsiveness, and contextual importance; and generating, by the screenless wearable device, a single vibration for each of the one or more reminders unless the one or more reminders are explicitly escalated.

9. The computer-implemented method of claim 1, wherein delivering the one or more reminders comprises at least one of:

triggering, by the screenless wearable device, the one or more reminders when a confidence threshold associated with the one or more contextual parameters is met; and intentionally delaying, by the screenless wearable device, the triggering of the one or more reminders until the one or more contextual parameters indicate an optimal context for delivery.

10. The computer-implemented method of claim 1, further comprising at least one of:

determining, by the screenless wearable device, an optimal location for the one or more reminders based on one or more historical patterns of the one or more users; and triggering, by the screenless wearable device, the one or more reminders when a location condition associated with the determined optimal location is satisfied, delivering, by the screenless wearable device, the one or more reminders comprising context-aware reminders based on the one or more contextual parameters associated with the one or more users, comprising at least one of: the location, time, movement status, physiological state, environmental conditions, and user behavior.

11. The computer-implemented method of claim 1, further comprising at least one of:

triggering, by the screenless wearable device, the one or more reminders at a next logical time when the one or more locations associated with the one or more reminders are missed by the one or more users;

suggesting, by the one or more communication devices, one or more reminder behaviors to the one or more users based on past compliance of the one or more users with previously delivered reminders; and generating, by the one or more communication devices, one or more gentle reminders tied to one or more recovery patterns of the one or more users.

12. The computer-implemented method of claim 1, further comprising at least one of:

monitoring, by the heart rate sensor of the screenless wearable device, one or more health parameters of the one or more users; and reviewing, by the one or more communication devices, at least one of: user activity, heart rate trend, and completed reminders, to suggest one or more recommendations to the one or more users for reaching one or more health goals.

13. The computer-implemented method of claim 1, further comprising at least one of:

discarding the audio, requesting a repeat capture of the audio, generating a tentative reminder for user confirmation through a companion application, and storing the one or more inputs temporarily for deferred reprocessing, when the audio is incomplete, unclear, noisy, and associated with an audio confidence score below a predefined threshold;

temporarily buffering the audio and extracted intent tokens, deferring reminder generation until connectivity is restored, performing at least partial local processing on at least one of: the screenless wearable device and the one or more communication devices, and generating a provisional reminder based on locally available code-word recognition, when an absence of an internet in the one or more communication devices;

storing the audio and compressed reminder-relevant data in local memory, retrying transmission upon re-establishment of the one or more communication devices, triggering a local fallback indication to the one or more users, and queuing reminder metadata for later synchronization, when a communication link between the screenless wearable device and the one or more communication devices is interrupted; and assigning a lower confidence state to the generated one or more reminders, routing the one or more reminders to a review queue within the companion application, requesting an optional user confirmation, re-ranking multiple candidate intents, and applying historical user behavior and contextual metadata to refine interpretation, when a wrong intent is detected.

14. A computer-implemented system for generating one or more reminders for one or more users using a screenless wearable device of the one or more users, the computer-implemented system comprising:

the screenless wearable device configured to:

obtain, by a transceiver of the screenless wearable device, one or more inputs from the one or more users through an input button;

activate, by a microcontroller unit (MCU) of the screenless wearable device, a microphone to execute a press-to-listen interaction in response to the one or more users providing the one or more inputs through the input button, wherein the microphone is active only for a pre-defined time duration upon receiving the one or more inputs;

capture, by the microphone of the screenless wearable device, natural speech of the one or more users during the pre-defined time duration;

analyze, by the MCU of the screenless wearable device, at least one of: one or more pre-defined code words and one or more phrases related to the one or more reminders from the captured natural speech; and transmit, by the transceiver of the screenless wearable device, an audio associated with the natural speech of the one or more users to one or more communication devices associated with the one or more users through one or more communication technologies, for processing the audio; and the one or more communication devices configured to generate the one or more reminders based on the audio associated with the natural speech of the one or more users, upon receiving the audio associated with the natural speech of the one or more users, using an artificial intelligence (AI) model; and the screenless wearable device further configured to deliver the generated one or more reminders to the one or more users through one or more haptic vibrations.

15. The computer-implemented system of claim 14, wherein in generating the one or more reminders based on the audio, the one or more communication devices are further configured to:

convert the audio associated with the natural speech of the one or more users, to one or more texts using automatic speech recognition (ASR) models for downstream text based AI analysis;

detect at least one of: one or more specific pre-defined code words from the converted one or more texts, using a trained lightweight AI model;

analyze the converted one or more texts to determine one or more user intents differentiating a casual statement and an actionable reminder request using one or more machine learning (ML) classifiers;

extract one or more named entities comprising at least one of: one or more items, people, one or more locations, and one or more time references, from the converted one or more texts, using named entity recognition (NER);

generate the one or more reminders by associating the extracted one or more named entities with the determined one or more user intents; and generate reminder metadata comprising at least one of: one or more reminder contents, assigned one or more locations, one or more trigger conditions, urgency level, and one or more sharing permissions.

16. The computer-implemented system of claim 14, upon generating the one or more reminders, the screenless wearable device is further configured to:

receive the reminder metadata from the one or more communication devices through the one or more communication technologies;

store, by the MCU of the screenless wearable device, the reminder metadata in an embedded flash memory, wherein the embedded flash memory is configured to store basic system data comprising at least one of: device state, the reminder metadata, and one or more vibration patterns;

continuously monitor one or more contextual parameters comprising at least one of: combination of a current location of the one or more users, time, movement status, and routine patterns, to determine whether the one or more trigger conditions associated with the one or more reminders are satisfied, wherein the combination of current location of the one or more users comprise at least one of: when the one or more users enter the one or more locations, when the one or more users exits the one or more locations, when the one or more users are on one or more routes towards the one or more locations, and when the one or more users stay at the one or more locations within a time-window;

determine, by a heart rate sensor of the screenless wearable device, a current state of the one or more users, wherein the current state of the one or more users comprises at least one of: busy, stressed, and driving, and wherein the screenless wearable device suppresses the one or more reminders based on the determined current state; and select, by the MCU of the screenless wearable device, one or more appropriate vibration patterns from the stored one or more vibration patterns based on at least one of: the urgency level of the one or more reminders and user preferences, wherein one or more vibration patterns indicate at least one of: urgency and follow-up reminders, adapting the one or more users to stay aware without being distracted.

17. The computer-implemented system of claim 14, wherein the screenless wearable device is further configured to implement privacy-preserving audio lifecycle, by at least one of:

buffering the natural speech with one or more intent-relevant keywords before transmitting the audio to the one or more communication devices;

discarding the natural speech with one or more non-relevant keywords before transmitting the audio to the one or more communication devices; and deleting data associated with the audio from the screenless wearable device when the audio is transmitted to the one or more communication devices.

18. The computer-implemented system of claim 14, wherein the one or more communication devices are further configured to at least one of:

adapt the one or more users to define a time duration for retaining the audio on at least one of: the one or more communication devices and a cloud, based on a user-configurable audio retention policy;

adapt the one or more users to share the one or more reminders with one or more second users while maintaining one or more private reminders restricted;

adapt a selective routing of the one or more reminders to one or more defined groups, wherein the one or more defined groups comprise at least one of: one or more family groups and one or more trusted groups;

adapt one or more reminder permissions based on one or more roles of the one or more users;

identify one or more intended recipients from the captured natural speech at the time of capturing the one or more reminders; and direct the one or more reminders to the identified one or more intended recipients.

19. The computer-implemented system of claim 14, wherein in delivering the one or more reminders through the one or more haptic vibrations, the screenless wearable device is configured to at least one of:

generate a stronger vibration only when the one or more reminders require increased user attention based on at least one of: the urgency level, user responsiveness, and contextual importance;

generate a single vibration for each of the one or more reminders unless the one or more reminders are explicitly escalated;

trigger the one or more reminders when a confidence threshold associated with the one or more contextual parameters is met; and intentionally delay the triggering of the one or more reminders until the one or more contextual parameters indicate an optimal context for delivery.

20. A non-transitory computer-readable storage medium having instructions stored therein that when executed by one or more hardware processors, cause the one or more hardware processors to execute operations of:

obtaining, by a transceiver microcontroller unit (MCU) of a screenless wearable device, one or more inputs from the one or more users through an input button;

activating, by a microcontroller unit (MCU) of the screenless wearable device, a microphone to execute a press-to-listen interaction in response to the one or more users providing the one or more inputs through the input button, wherein the microphone is active only for a pre-defined time duration upon receiving the one or more inputs;

capturing, by the microphone of the screenless wearable device, natural speech of the one or more users during the pre-defined time duration;

analyzing, by the MCU of the screenless wearable device, at least one of: one or more pre-defined code words and one or more phrases related to the one or more reminders from the captured natural speech;

transmitting, by a transceiver of the screenless wearable device, an audio associated with the natural speech of the one or more users to one or more communication devices associated with the one or more users through one or more communication technologies, for processing the audio;

upon receiving the audio associated with the natural speech of the one or more users, generating, by the one or more communication devices, the one or more reminders based on the audio associated with the natural speech of the one or more users, using an artificial intelligence (AI) model; and delivering, by the screenless wearable device, the generated one or more reminders to the one or more users through one or more haptic vibrations.

* * * * *